(12) United States Patent
Giglia et al.

(10) Patent No.: US 10,151,679 B2
(45) Date of Patent: Dec. 11, 2018

(54) ENHANCED AEROSOL TEST FOR ASSESSING FILTER INTEGRITY

(71) Applicant: EMD Millipore Corporation, Burlington, MA (US)

(72) Inventors: Salvatore Giglia, Burlington, MA (US); David Nhiem, Burlington, MA (US); Gabriel Tkacik, Burlington, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 15/057,641

(22) Filed: Mar. 1, 2016

(65) Prior Publication Data

US 2016/0299048 A1    Oct. 13, 2016

Related U.S. Application Data

(60) Provisional application No. 62/144,553, filed on Apr. 8, 2015.

(51) Int. Cl.
    *G01N 15/08* (2006.01)
    *B01D 65/10* (2006.01)
    *G01M 3/20* (2006.01)

(52) U.S. Cl.
    CPC ......... *G01N 15/088* (2013.01); *B01D 65/102* (2013.01); *G01M 3/20* (2013.01); *G01N 15/0826* (2013.01); *B01D 2273/18* (2013.01); *G01N 2015/084* (2013.01); *G01N 2015/0846* (2013.01)

(58) Field of Classification Search
    CPC .... G01N 15/0088; B01D 65/102; G01M 3/20

USPC ............................................................. 73/38
See application file for complete search history.

(56) References Cited

U.S. PATENT DOCUMENTS

| | | | |
|---|---|---|---|
| 3,395,514 | A | 8/1968 | Bub |
| 4,146,025 | A | 3/1979 | Warncke et al. |
| 4,213,768 | A | 7/1980 | Bauman et al. |
| 4,515,007 | A | 5/1985 | Herman |
| 4,619,136 | A | 10/1986 | Ortiz |

(Continued)

FOREIGN PATENT DOCUMENTS

| | | |
|---|---|---|
| CN | 103282107 A | 9/2013 |
| DE | 3520356 A1 | 12/1986 |

(Continued)

OTHER PUBLICATIONS

Translation of Yamamura JP 2013170927.*

(Continued)

*Primary Examiner* — Natalie Huls
*Assistant Examiner* — Monica S Young
(74) *Attorney, Agent, or Firm* — Nields, Lemack & Frame, LLC

(57) ABSTRACT

A method of aerosol integrity testing of filters, capable of detecting single defects that are less than 20 μm in diameter, and even as small as 2 μm in diameter, in liquid sterilizing grade filters such as filter cartridges. The method challenges the filter in a dry state with a particle stream of aerosol particles of the appropriate size and in the appropriate concentration, such that at least one or more of the particles in the stream will penetrate a defective region or regions within the membrane but will not penetrate in the integral region of the membrane. Wetting of the filter is not required.

27 Claims, 5 Drawing Sheets

(56) References Cited

U.S. PATENT DOCUMENTS

| | | | |
|---|---|---|---|
| 4,875,360 A | | 10/1989 | Ziemer |
| 4,914,957 A | | 4/1990 | Dougherty |
| 5,731,164 A | * | 3/1998 | Becker .................. A61L 2/022 |
| | | | 210/637 |
| 6,327,893 B1 | * | 12/2001 | Choi .................... B01D 46/16 |
| | | | 210/489 |
| 6,364,923 B1 | | 4/2002 | Wiedmeyer et al. |
| 7,186,286 B2 | | 3/2007 | Morse |
| 7,658,787 B2 | | 2/2010 | Morse et al. |
| 7,694,548 B2 | * | 4/2010 | Masset ................. G01N 17/002 |
| | | | 239/289 |
| 8,151,630 B1 | | 4/2012 | Gardner et al. |
| 2005/0050943 A1 | | 3/2005 | Barber et al. |
| 2009/0056547 A1 | | 3/2009 | Huza et al. |
| 2012/0006202 A1 | | 1/2012 | Morse et al. |
| 2012/0246910 A1 | | 10/2012 | Morse et al. |
| 2013/0186179 A1 | | 7/2013 | Osborne |
| 2013/0192344 A1 | * | 8/2013 | Bryan .................. B01D 65/102 |
| | | | 73/38 |

FOREIGN PATENT DOCUMENTS

| | | | |
|---|---|---|---|
| DE | 29709726 U1 | | 9/1997 |
| DE | 102011106512 A1 | | 1/2013 |
| EP | 0569754 A1 | | 11/1993 |
| EP | 1775015 A1 | | 4/2007 |
| EP | 2196250 A2 | | 6/2010 |
| GB | 1119623 A | | 7/1968 |
| JP | 58-210819 A | | 12/1983 |
| JP | 2013-170927 A | | 9/2013 |
| JP | 2013170927 A | * | 9/2013 |
| JP | 2014-500139 A | | 1/2014 |
| WO | 2007/021333 A2 | | 2/2007 |
| WO | 2012/064751 A2 | | 5/2012 |
| WO | 2012/106149 A2 | | 8/2012 |

OTHER PUBLICATIONS

European communication dated Aug. 17, 2016 in corresponding European patent application No. 16162802.9.

Japanese communication, with English translation, dated Feb. 21, 2017 in corresponding Japanese patent application No. 2016-076757.

Arunkumar et al, "High-efficiency particulate air filter test stand and aerosol generator for particle loading studies," Review of Scientific Instruments, vol. 78, Iss. 8, Aug. 2007.

Brosseau et al, "Collection Efficiency of Respirator Filters Challenged with Monodisperse Latex Aerosols," American Industrial Hygiene Association Journal, vol. 50, Iss. 10, pp. 544-549, Oct. 1989.

Brown et al, "Penetration of Test Aerosols Through Filters Described in Terms of a Gamma Distribution of Layer Efficiencies," Journal of Aerosol Science, vol. 18, Iss. 5, pp. 499-509, Oct. 1987.

Duberstein et al, "Sterile Filtration of Gases: A Bacterial Aerosol Challenge Test," Journal of the Parenteral Drug Association, vol. 32, No. 4, pp. 192-198, 1978.

Heidam et al, "On-Site Test of High-Efficiency Filters in Nuclear Facilities Using Radioactively Labelled Sodium Chloride (24Na)-Aerosol and Methyliodide (131I)," Journal of Aerosol Science, vol. 15, Iss. 3, p. 347, 1984.

Huang et al, "Ultrafine Aerosol Penetration through Electrostatic Precipitators," Environmental Science and Technology, vol. 36, No. 21, pp. 4625-4632, 2002.

Jornitz et al, "Filtration and Purification in the Biopharmaceutical Industry," Second Edition, vol. 174, Informa Healthcare, 2007.

Leahy et al, "Sterile Filtration of Gases by Membrane Filters," Biotechnology and Bioengineering, vol. 26, pp. 836-842, Aug. 1984.

Ling et al, "Measurement of Retention Efficiency of Filters against Nanoparticles in Liquids using an Aerosolization Technique," Environmental Science and Technology, vol. 44, No. 2, pp. 774-779, 2010.

Lowry et al, "Comparison of a sodium chloride aerosol filter test method to silica-dust and silica-mist filter test methods," American Industrial Hygiene Association Journal, vol. 39, No. 9, pp. 709-716, 1978.

Parker Hannifin Corporation, Integrity Testing Application Support Publication, AS_03_09/11 Rev. 1A., 2011.

"Sterilizing Filtration of Gases," Technical Report No. 40, PDA Journal of Pharmaceutical Science & Technology, vol. 58, pp. 7-44, Jan./Feb. 2005.

Qian et al, "Performance of N95 Respirators: Filtration Efficiency for Airborne Microbial and Inert Particles," American Industrial Hygiene Association Journal, vol. 59, No. 2, pp. 128-132, Feb. 1998.

Schuster et al, "Tandem HEPA filter tests," American Industrial Hygiene Association Journal, vol. 39, Iss. 2, pp. 144-150, 1978.

Strom et al, "In-Place Testing of Monitors for Airborne Reactor Effluents," International Atomic Energy Agency Proceeding Series, pp. 319-330, 1978.

Sugden et al, "A closed system for the filtration of Mycobacterium bovis liquid cultures using disposable capsule filters," Letters in Applied Microbiology, vol. 24, pp. 340-342, 1997.

Yavorsky, "Pod filter design enables integrity testing of large area depth filters," Next Generation Pharmaceuticals, Issue 4, 2005.

McBurnie et al., "Validation of Sterile Filtration", Pharmaceutical Technology, Filtration 2004, pp. s13-s23.

Korean communication, with English translation, dated Apr. 11, 2018 in corresponding Korean patent application No. 10-2018-0018187.

Altmann et al., "A New Method for Testing the Integrity of Membrane Modules," F & S Filtrieren und Separieren, vol. 11, Issue 5, 1997.

Chinese communication, with English translation, dated Oct. 8, 2018 in corresponding Chinese patent application No. 201610212653.5.

Xu et al., "Excellent Functional Membranes", High Technology Popular Science Series, Gansu Science and Technology Press, 2012.

Zhang et aL, "Membrane Water Treatment Experiments", General Higher Education Textbook under "Twelfth Five Year Plan" Ministry Level Planning Program (for undergraduate course), China Textile and Apparel Press, 2015.

* cited by examiner

ENHANCED AEROSOL TEST FOR ASSESSING FILTER INTEGRITY

This application claims priority of U.S. Provisional Application Ser. No. 62/144,553 filed Apr. 8, 2015, the disclosure of which is incorporated herein by reference.

FIELD OF THE DISCLOSURE

The present disclosure generally relates to a method for integrity testing filters, such as liquid sterilizing grade filters.

BACKGROUND

High purity filtration of media, such as in the fields of biotechnology, chemistry, electronics, pharmaceuticals, and the food and beverage industries requires the use of sophisticated filter modules that are not only capable of a high degree of separation, but that will tend to prevent contamination of the environment, of the medium to be filtered, and of the resulting filtrate. This is designed to prevent unwanted, often dangerous organisms, such as bacteria or viruses, as well as environmental contaminants, such as dust, dirt, and the like from entering into the process stream and end product. To ensure sterility of the filtrate, filter modules must maintain their integrity throughout the filtration process. Accordingly, integrity testing of sterilizing filters is a fundamental requirement of critical process filtration applications in the pharmaceutical industry, and is used to identify filters containing oversized pores or defects that can compromise the retention performance of the filter. FDA guidelines recommend integrity testing of filter modules prior to use and after filtration. Typically this testing is initially performed after steam sterilization to ensure that the filter is not damaged; accordingly, care must be taken to ensure that sterility of the filter, and thus the filtrate, is not compromised. Post-processing, the filter integrity test is performed again in situ to detect whether the filter was compromised during use. This information can be used to alert operators to a potential problem immediately after processing, and to quickly take corrective action. Further, FDA guidelines require that integrity testing documentation be included with batch product records.

There are a variety of methods of integrity testing, including the diffusion test and the pressure hold test. The diffusion test measures the rate of gas transfer through a filter to be tested. At differential gas pressures below the bubble point, gas molecules migrate through water-filled pores of a wetted membrane following Fick's Law of Diffusion. The gas diffusional flow rate for a filter is proportional to the differential pressure and the total surface area of the filter. At a pressure approximately 80% of the minimum bubble point, the gas which diffuses through the filter membrane can be measured to determine a filter's integrity. A diffusional flow reading exceeding a value stated by the manufacturer indicates a variety of problems, including an incorrect temperature, wrong pore size, incompletely wetted membrane, non-integral membrane or seal, or inadequate stabilization time. The pressure hold test, also known as the pressure decay or pressure drop test, is a variation of the diffusion test. In this test, a highly accurate gauge is used to monitor upstream pressure changes due to gas diffusion through the filter. Because there is no need to measure gas flow downstream of the filter, any risk to downstream sterility is eliminated.

These tests require that the filter be wetted, which is a time and water-consuming process. The sensitivity of these tests is also limited in part due to background noise inherent in these tests.

Compared to traditional integrity tests such as gas/liquid diffusion, aerosol integrity testing has a number of advantages including fast test times, and no required wetting of the filter. Aerosol integrity testing has been used in the pharmaceutical industry for detecting defects in HEPA and ULPA grade filters. This test is also used for filters providing sterile gas. However, there are no known applications of aerosol testing to assess the integrity of filters for sterilizing liquids. Aerosol integrity testing has been considered to be unsuitable for liquid filters because particle capture in gases can occur by a number of mechanisms that are not functional in liquids. Mechanisms such as electrostatic attraction and diffusional deposition can result in interception of particles in a filter element, so that penetration of particles through defects is not assured. While aerosol integrity testing has been demonstrated to reliably detect relatively large defects (>100 µm), it has not been previously known how to detect defects on the order of 20 µm or less; i.e., defects that could compromise the retention performance of a liquid sterilizing grade filter. Liquid sterilizing grade filters are defined in the FDA "Aseptic Guideline" (FDA "Guideline on Sterile Drug Products Produced by Aseptic Processing", Division of Manufacturing and Product Quality, Rockville, Md., June 1987) as those capable of totally retaining a B. diminuta challenge level of $10^7$ cfu/cm$^2$ at a differential pressure of 30 psi.

It therefore would be desirable to provide a methodology for aerosol testing of filters that does not suffer from the drawbacks of the prior art.

SUMMARY

The problems of the prior art are addressed by the embodiments disclosed herein, which relate to an aerosol integrity test of filters. In certain embodiments, the method is capable of detecting single defects that are less than 20 µm in diameter, and even as small as 2 µm in diameter, in liquid sterilizing grade filters, such as liquid sterilizing grade filter cartridges, for example. The test can be carried out without destroying the filter. Since the filter need not be wetted, it also need not be dried upon completion of the test. In certain embodiments, the method includes generating aerosol particles of the appropriate size and in the appropriate concentration, challenging the filter with the particle stream at a condition such that at least one or more of the particles in the stream will penetrate a defective region or regions within the membrane but will not penetrate in the integral region of the membrane, and detecting any particles that penetrate a defective region. Because an integral filter will not exhibit any particle passage, the detection of only a single or a few particles indicates a defect.

In accordance with certain embodiments, the method allows for the non-destructive integrity testing of a sterilizing grade filter in a dry state. In certain embodiments, the method achieves a higher defect detection sensitivity than conventional aerosol tests and conventional gas/liquid diffusion and bubble point tests. In certain embodiments, the method allows for faster integrity testing than conventional methods. In certain embodiments, the filter is a pleated filter.

BRIEF DESCRIPTION OF THE DRAWINGS

For a better understanding of the present disclosure, reference is made to the accompanying drawings, which are incorporated herein by reference and in which.

DETAILED DESCRIPTION

Figure 1:
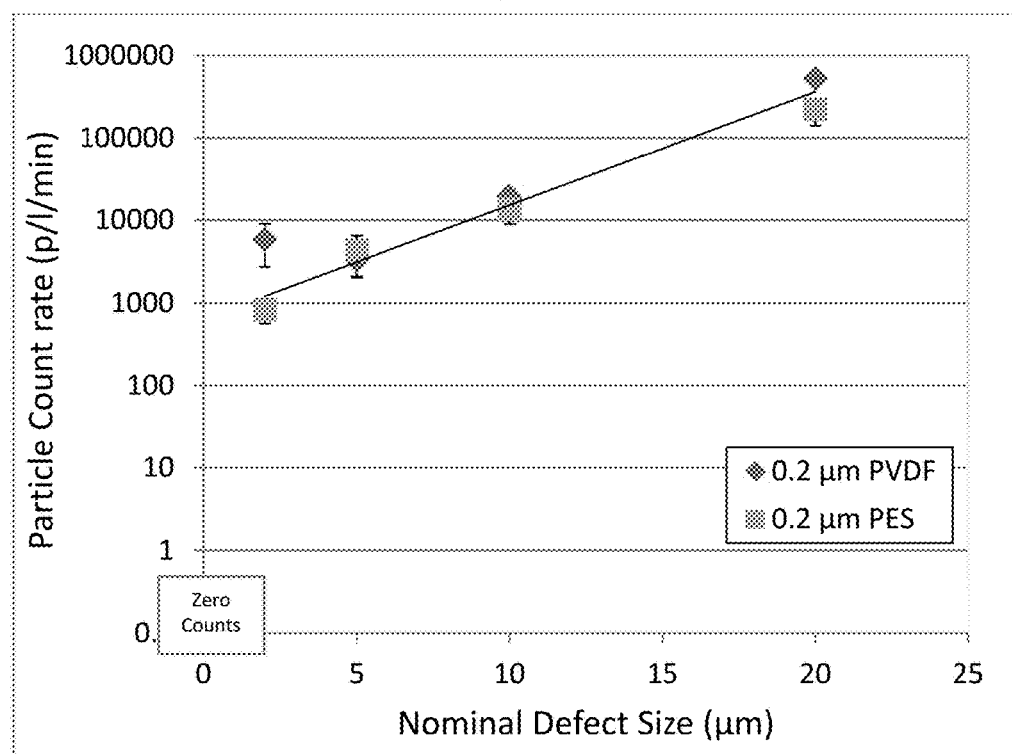
FIG. 1 is a graph of particle count rate vs. nominal defect size for various membranes.

The sensitivity of an integrity test is constrained by its ability to differentiate the signal for a defect from any background noise that can compete or interfere with the signal. For example, for the conventional air diffusion integrity test that is commonly used to assess the integrity of sterilizing grade liquid filters, even perfectly integral filters will exhibit a significant diffusion flow rate through the liquid layer in the filter. This diffusive flow rate is sensitive to filter thickness, filter porosity, pore tortuosity, and operating condition variables such as temperature and test pressure. A defect in the filter will allow for a convective flow rate in excess of the diffusion flow rate but this excess flow rate must be high enough to be clearly distinguishable from the typical range of diffusion flow rates in integral devices. For small defects, the convective flow rate through a defect can be masked by the diffusional flow through the integral portion of the filter.

Ideally, the background noise in an integrity test is as close to zero as possible. In the case of aerosol testing, the number of particles that are able to penetrate an integral filter should be zero, so that the detection of any particle that has penetrated a filter is an unambiguous signal for a defect.

It has been found that sterilizing grade filters (often designated as 0.22 µm rated filters) retain 100% of aerosol particles in the size range between about 10 nm and 800 nm. In certain embodiments, suitable particles include NaCl particles, KCl particles, as well as other materials that are commonly used to generate aerosols. Other common materials include di(2-ethylhexyl) phthalate (DOP), polystyrene (PSL) and polystyrene-divinylbenzene (PS-DVB) latex spheres, and powders and dusts such as silica, uranium-dioxide, coal, carbon black, pollens, and Arizona road dust (ARD).

Table 1 below shows particle penetration as a function of particle size for PVDF membranes with nominal pore size ratings between 0.1 and 5 µm:

TABLE 1

| PVDF Membrane | Pore Rating (µm) | Cumulative Particle Penetration (%) |
|---|---|---|
| Sample 1 | 0.1 | 0 |
| Sample 2 | 0.2 | 0 |
| Sample 3 | 0.45 | 0 |
| Sample 4 | 0.65 | 0 |
| Sample 5 | 1 | 0.0000089 |
| Sample 5 | 5 | 1.2 |

Aerosol solution: 0.1 g/l NaCl
Aerosol Inlet concentration: 6.5x × $10^6$ p/cc

It can be seen that for membranes with nominal pore size rating less than about 1 µm, the retention efficiency is 100%.

If a defect exists however, then particles smaller than the defect size will have the potential to penetrate the filter.

In accordance with certain embodiments, the method of integrity testing a filter includes providing a liquid sterilizing grade filter to be tested, wherein the filter is not pre-wetted (dry); generating an aerosol particle stream wherein the particles in the stream have a suitable size and a suitable concentration to challenge the filter and penetrate a defective region in the filter without penetrating integral regions in the filter; applying the aerosol stream to the filter for a predetermined period of time, and detecting particles that penetrate the defective region. For sterilizing grade filters, suitable particle concentrations may be in the range $10^5$ to $10^7$ particles/cm$^3$, and particle sizes may be in the range 10-1000 nm in diameter. In certain embodiments, the method is able to detect single defects that are less than 20 µm in diameter, and as small as 2 µm in diameter. In certain embodiments, one or more of the solids concentration of the particle stream (typically $10^5$-$10^7$ particles/cm$^3$), the pressure at which the aerosol is created (typically 5-60 psig), and the number of atomizer generators (from 1 to 6, for example) is modified to ensure passage of particles through defects. In certain embodiments, the amount of time the aerosol particle stream is applied to the filter is modified to allow for sufficient resolution of small rates of particle passage. For example, if the rate of particles that penetrate the membrane is less than one particle per minute, then several minutes can be allowed to ensure that the particle passage rate is accurately determined. With respect to particle concentration, pressure, number of atomizers, and length of time the aerosol stream is applied, these parameters are determined for each type of filter, and can then be applied for all filters of that type.

In certain embodiments, the filters are pleated filters, such as PVDF pleated filters. Pleated filters are typically made with the filter media folded in an accordion-like fashion. The filters may be spiral pleated filters. The filter element may be a membrane. In certain embodiments, the filters, such as pleated filters, are housed in a cartridge.

Example 1

Figure 8:
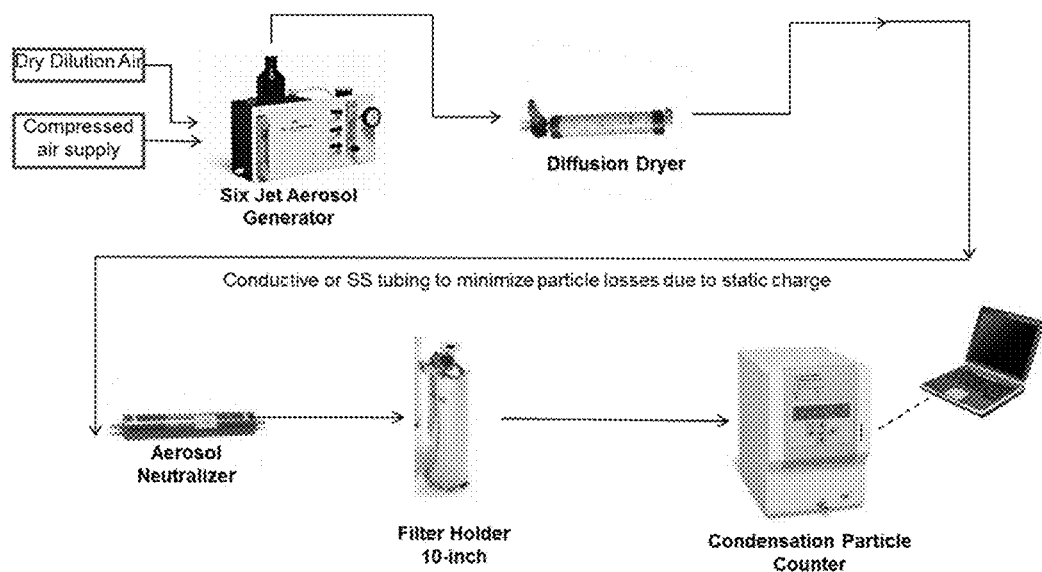
FIG. 8 is a schematic diagram showing a test setup in accordance with certain embodiments.

In order to assess the capability of the aerosol test to identify defective filters, cylindrical holes of sizes between 2 µm and 20 µm were laser drilled into 142-mm membrane discs. Two types of membranes were evaluated: a 0.2 µm rated sterilizing grade PVDF membrane and a 0.2 µm rated sterilizing grade PES membrane. These membrane filters were challenged with a NaCl aerosol stream (0.12 g/1 NaCl, 3×$10^6$p/cc aerosol inlet concentration) generated using a TSI model 3076 aerosol generator at test conditions recommended by the aerosol equipment supplier. The aerosol generator pressure was set at 30 psig and the particles were counted for one minute. The aerosol particles were counted using a TSI model 3772 condensation particle counter. A suitable test set up is shown in FIG. 8. FIG. 1 shows that while the integral membrane showed no passage of particles, the membranes with the laser hole defects showed very high passage of particles. This test demonstrates that particles could readily pass through the defects and be detected by the particle counter. The integral membranes did not exhibit any particle passage.

Example 2

Figure 2:
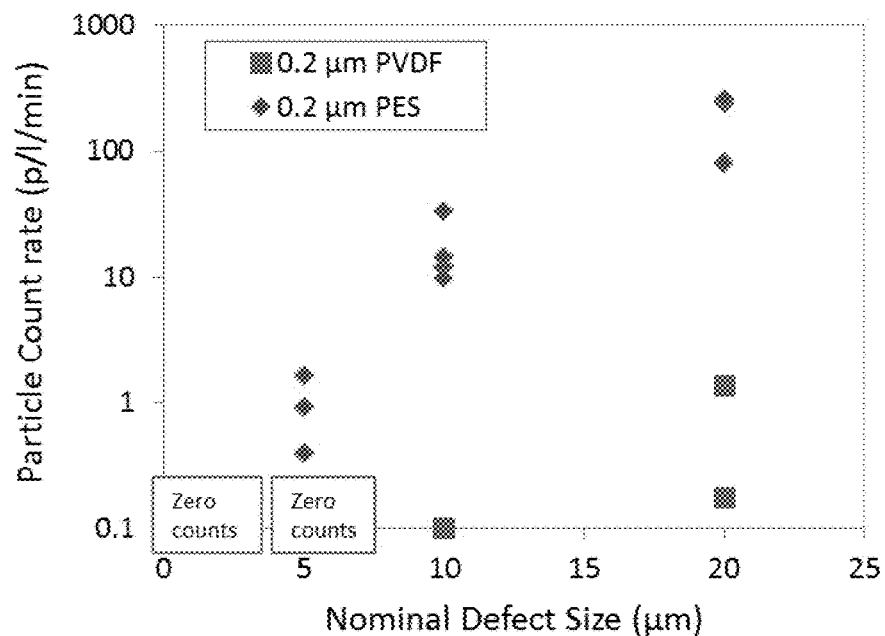
FIG. 2 is a plot of particle count rate vs. nominal defect size.
Figure 3:
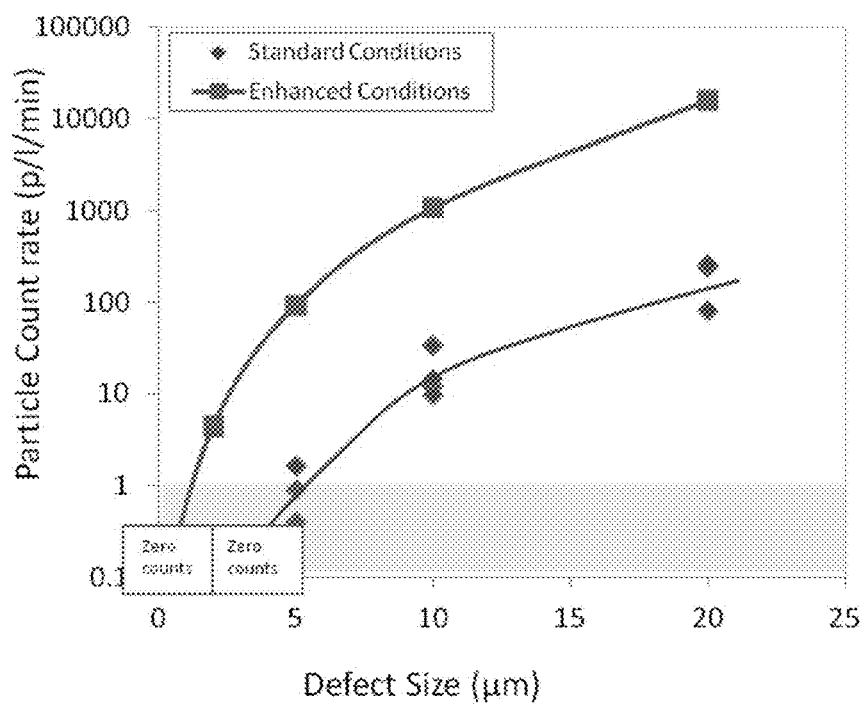
FIG. 3 is a graph of particle count rate vs. defect size for a PES membrane.
Figure 4:
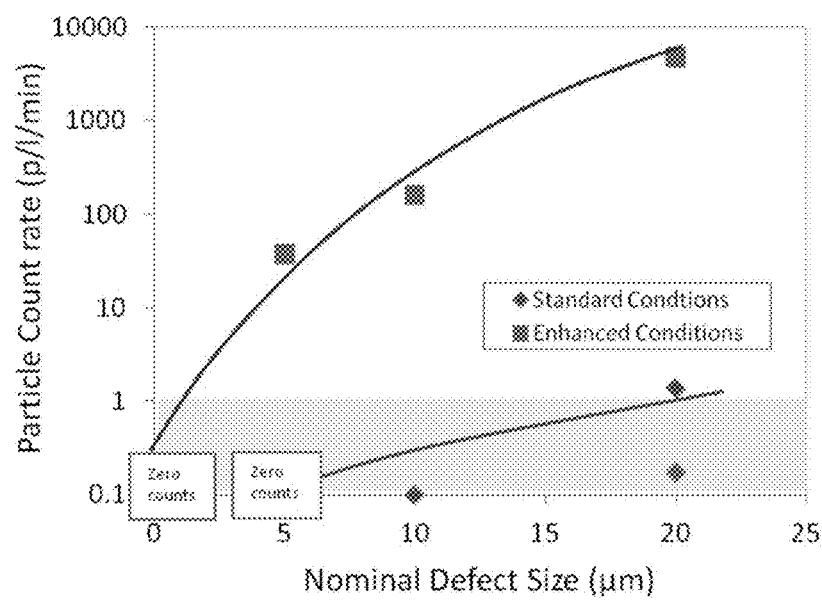
FIG. 4 is a graph of particle count rate vs. defect size for a PVDF membrane.
Figure 5:
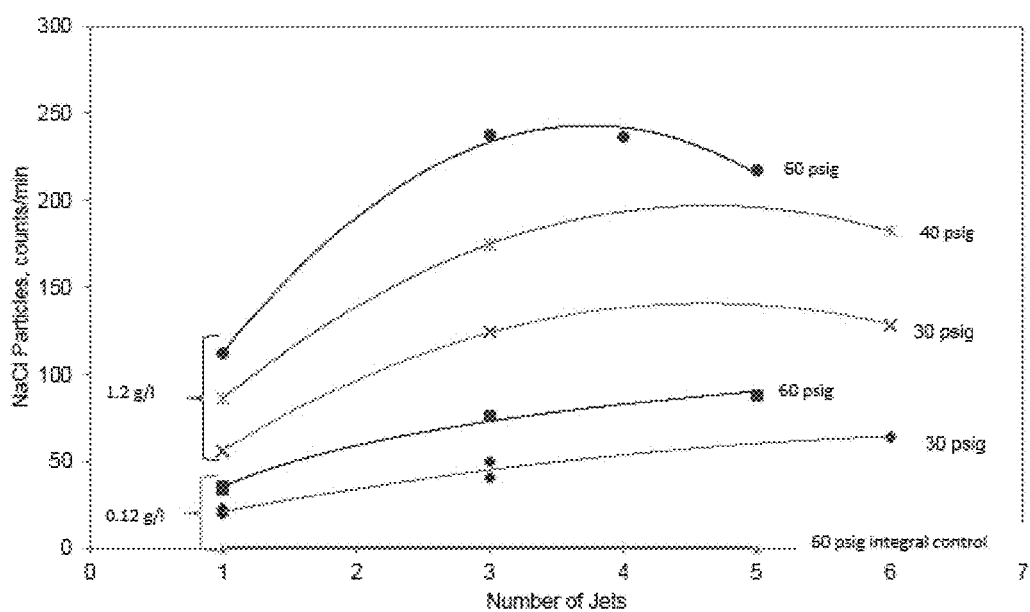
FIG. 5 is a graph of NaCl particle counts vs. number of atomizer jets.

Sterilizing grade membranes in pleated cartridge format were tested under the same conditions, including aerosol and test pressure, as the 142 mm discs described in Example 1. As was done with the 142 mm discs, pleated 10" cartridges were constructed with membranes containing single laser hole defects between 2 μm and 20 μm. It can be seen from FIG. 2 that in pleated cartridge format, the defect signal was much reduced compared to flat discs. Defect sizes that were easily detected in 142 mm discs (containing about 127 cm$^2$ of membrane area) format were not detectable in 10" pleated cartridge (containing about 5000 cm$^2$ of membrane area) format. No particle penetration was detected in the PES membrane cartridge containing a 2 μm hole, or, in a PVDF membrane cartridge containing a 5 μm hole. This was in part due to the more tortuous pathway that the particles must travel in a pleated membrane, which also contains porous upstream and downstream support layers. The tortuous pathway hinders access to the membrane surface, and therefore increases the opportunity for particle interception either upstream or downstream of the defect and upstream of the particle detector. In addition, as membrane area increases, the flow through the defect becomes an increasingly smaller portion of the flow through the entire membrane and therefore there is a dilution effect on the measured downstream sample.

To overcome the low passage of particles through small defects in 10" pleated membrane filters, the concentration and flow rate of particles challenging the filter were increased. Particle concentration can be increased by increasing the solids concentration in the atomizer solution, increasing the pressure at which the aerosol is created, and increasing the number of atomizer generators. In addition, the test was run for at least 5 minutes to allow for sufficient resolution of small rates of particle passage. This is in contrast to the typical practice of aerosol testing in which the test is often terminated in one minute or less. An enhanced combination of aerosol test conditions were developed and are summarized in Table 2:

TABLE 2

| Condition | Number of Atomizers | NaCl Concentration (w/w %) | Atomizer Pressure (psig) |
|---|---|---|---|
| Standard | 1 | 0.012 | 30 |
| Enhanced | 5 | 1.2 | 50 |

TABLE 3

| Membrane Type | Particle Type | Defect Size (μm) | Particle Penetration Rate (p/l/min) |
|---|---|---|---|
| PES | NaCl | None | <1 |
|  |  | 5 | 148 |
|  | KCl | None | <1 |
|  |  | 5 | 180 |
| PVDF | NaCl | None | <1 |
|  |  | 5 | 215 |
|  | KCl | None | <1 |
|  |  | 5 | 273 |

Example 3

Figure 6:
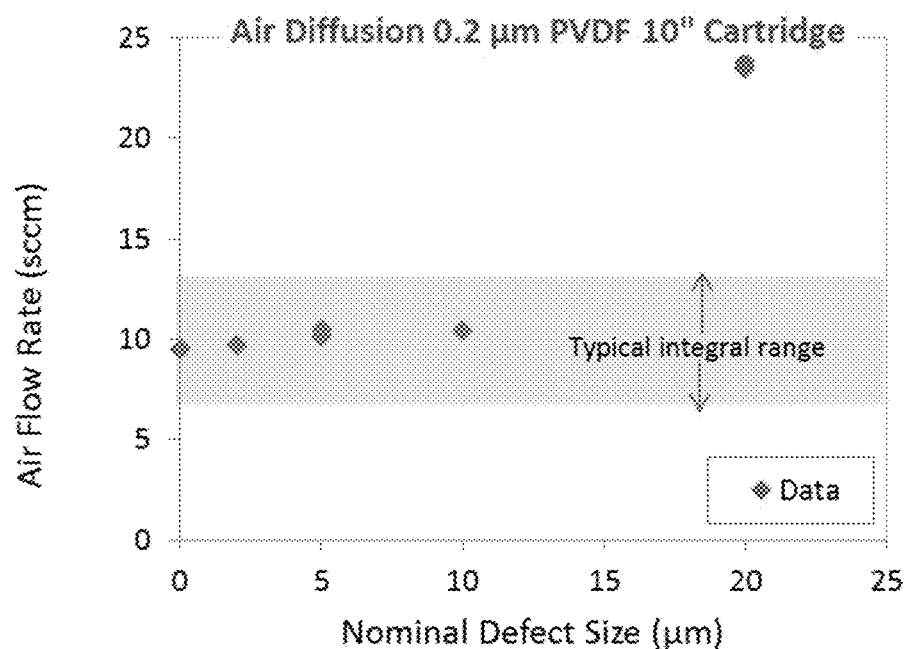
FIG. 6 is a plot of air flow rate vs. nominal defect size.
Figure 7:
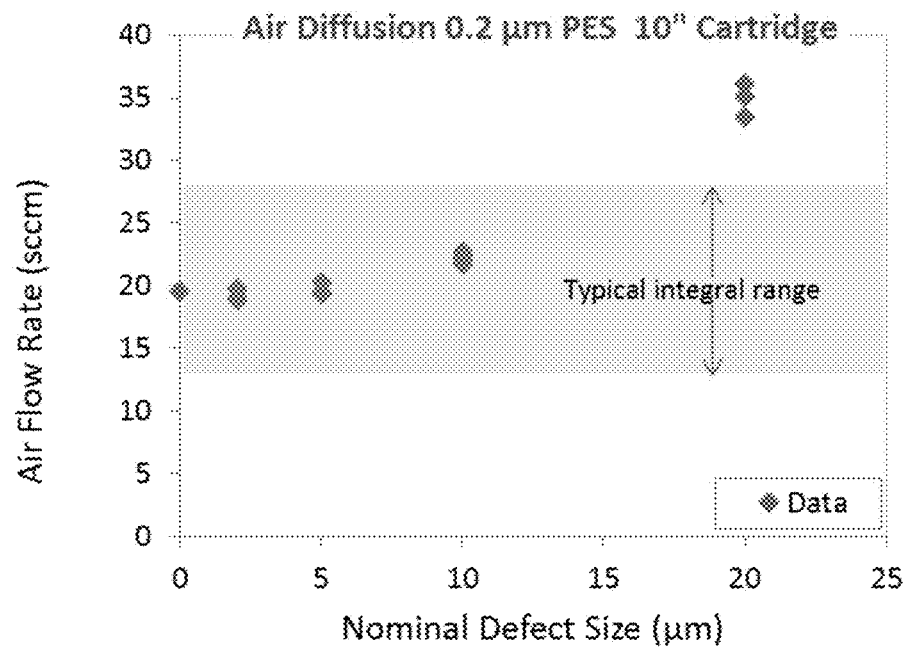
FIG. 7 is another plot of air flow rate vs. nominal defect size.

The PES and PVDF membrane cartridges were also tested using a standard air diffusion integrity test. The cartridges were wetted and then the air diffusion flow rate was measured using a test pressure of 40 psig. FIGS. 6 and 7 show that while the air diffusion flow rate was slightly elevated for cartridges containing defects smaller than about 10-15 μm compared to the integral controls, the increase in flow rate was not enough to differentiate integral from non-integral devices. Typical flow rate ranges of integral cartridges is indicated by the shaded areas in the plots. Defects less than 20 microns could not be detected.

What is claimed is:

1. A method of integrity testing a filter in the dry state, comprising:
   providing a liquid sterilizing grade filter to be tested in a dry state, wherein said liquid sterilizing grade filter is a filter capable of totally retaining a B. diminuta challenge level of 10$^7$ cfu/cm$^2$ at a differential pressure of 30 psi;
   generating an aerosol particle stream at a pressure of at least 5 psig, wherein the particles in said stream have a suitable size and a suitable concentration to challenge said filter and penetrate any defective region in said filter but will not penetrate integral regions in said filter, wherein said concentration of said particles in said stream is at least 10$^3$ particles/cm$^3$; and
   detecting particles that penetrate said defective region.

2. The method of claim 1, wherein defects in said filter that are as small as 2 microns are detected by said step of detecting particles that penetrate said defective region.

3. The method of claim 1, wherein said filter is pleated.

4. The method of claim 3, wherein said aerosol particle stream is generated with a plurality of atomizers at a pressure of 50 psig.

5. The method of claim 1, wherein said filter is housed in a cartridge.

6. The method of claim 1, wherein said aerosol particle stream comprises NaCl.

7. The method of claim 1, wherein said filter is a PVDF filter.

8. The method of claim 1, wherein said filter is a PES filter.

9. The method of claim 1, wherein said particles in said aerosol particle stream have a size and concentration to penetrate a defect less than 20 μm in diameter in said filter.

10. The method of claim 1, wherein the aerosol particle stream is generated at a pressure of 5-60 psig.

11. The method of claim 1, wherein said aerosol particle stream is generated by a plurality of atomizers.

12. The method of claim 1, wherein the particles in said stream have a concentration of 10$^6$ particles/cm$^3$.

13. The method of claim 1, wherein the particles in said stream have a concentration in the range of 10$^5$-10$^7$ particles/cm$^3$.

14. The method of claim 1, wherein said filter is a 0.2 μm rated filter.

15. A method of integrity testing a filter in the dry state, comprising:
   providing a liquid sterilizing grade filter to be tested in a dry state, wherein said liquid sterilizing grade filter is a filter capable of totally retaining a B. diminuta challenge level of 10$^7$ cfu/cm$^2$ at a differential pressure of 30 psi;
   generating an aerosol particle stream with at least one atomizer at a pressure of at least 5 psig, wherein the particles in said stream have a concentration of at least 10$^3$ particles/cm$^3$ and have a size effective to penetrate a defect less than 20 μm in diameter if present in said filter but not effective to penetrate integral regions in said filter;
   challenging said filter with said aerosol particle stream;

providing a particle detector downstream of said liquid sterilizing grade filter to detect any particles that penetrate said defect if present in said filter; and classifying said filter as non-integral if a particle is detected by said particle detector, and classifying said filter as integral if no particles are detected by said particle detector.

16. The method of claim 15, wherein the particles in said stream have a size effective to penetrate a defect less than 2 μm in diameter if present in said filter.

17. The method of claim 15, wherein said filter is pleated.

18. The method of claim 17, wherein said aerosol particle stream is generated with a plurality of atomizers at a pressure of 50 psig.

19. The method of claim 15, wherein said filter is housed in a cartridge.

20. The method of claim 15, wherein said aerosol particle stream comprises NaCl.

21. The method of claim 15, wherein said filter is a PVDF filter.

22. The method of claim 15, wherein said filter is a PES filter.

23. The method of claim 15, wherein the aerosol particle stream is generated at a pressure of 5-60 psig.

24. The method of claim 15, wherein said aerosol particle stream is generated by a plurality of atomizers.

25. The method of claim 15, wherein the particles in said stream have a concentration of $10^6$ particles/cm$^3$.

26. The method of claim 15, wherein the particles in said stream have a concentration in the range of $10^3$-$10^7$ particles/cm$^3$.

27. The method of claim 15, wherein said filter is a 0.2 μm rated filter.

* * * * *

UNITED STATES PATENT AND TRADEMARK OFFICE
CERTIFICATE OF CORRECTION

PATENT NO. : 10,151,679 B2
APPLICATION NO. : 15/057641
DATED : December 11, 2018
INVENTOR(S) : Salvatore Giglia et al.

Page 1 of 1

It is certified that error appears in the above-identified patent and that said Letters Patent is hereby corrected as shown below:

In the Claims

In Column 6, Line 22, in Claim 1 delete "$10^3$" and insert -- $10^5$ --, therefor.

In Column 6, Line 63, in Claim 15 delete "$10^3$" and insert -- $10^5$ --, therefor.

In Column 8, Line 13, in Claim 26 delete "$10^3$" and insert -- $10^5$ --, therefor.

Signed and Sealed this
Fourteenth Day of May, 2019

Andrei Iancu
*Director of the United States Patent and Trademark Office*